US009267828B2

(12) United States Patent
Ono et al.

(10) Patent No.: US 9,267,828 B2
(45) Date of Patent: Feb. 23, 2016

(54) FLUID FLOW RATE DETECTION DEVICE (71) Applicants: THE UNIVERSITY OF TOKYO, Tokyo (JP); HITACHI ALOKA MEDICAL, LTD., Tokyo (JP)

(72) Inventors: Minoru Ono, Tokyo (JP); Keiichi Itatani, Kanagawa (JP); Takashi Okada, Tokyo (JP)

(73) Assignees: THE UNIVERSITY OF TOKYO, Tokyo (JP); HITACHI ALOKA MEDICAL, LTD., Tokyo (JP)

( * ) Notice: Subject to any disclaimer, the term of this patent is extended or adjusted under 35 U.S.C. 154(b) by 0 days.

(21) Appl. No.: 14/383,540

(22) PCT Filed: Oct. 17, 2012

(86) PCT No.: PCT/JP2012/076810
§ 371 (c)(1),
(2) Date: Sep. 5, 2014

(87) PCT Pub. No.: WO2013/136573
PCT Pub. Date: Sep. 19, 2013

(65) Prior Publication Data
US 2015/0013471 A1    Jan. 15, 2015

(30) Foreign Application Priority Data

Mar. 16, 2012  (JP) .................................. 2012-060973

(51) Int. Cl.
*G01F 1/66*        (2006.01)
*A61B 8/06*        (2006.01)
(Continued)

(52) U.S. Cl.
CPC ... *G01F 1/66* (2013.01); *A61B 8/06* (2013.01); *A61B 8/488* (2013.01); *G01S 15/8984* (2013.01)

(58) Field of Classification Search
None
See application file for complete search history.

(56) References Cited

U.S. PATENT DOCUMENTS 4,664,122 A * 5/1987 Yano ...................... A61B 8/463
                                                 600/425
5,769,079 A * 6/1998 Hossack .................. A61B 8/06
                                                 600/454

(Continued)

FOREIGN PATENT DOCUMENTS

CN       1960677 A     5/2007
JP    2005-21347 A     1/2005

(Continued)

OTHER PUBLICATIONS

International Search Report for PCT/JP2012/076810, Jan. 8, 2013.

(Continued)

*Primary Examiner* — Harshad R Patel (57) ABSTRACT

To provide a fluid flow rate detection device which can be evaluated as adequate from a medical point of view. The velocity of a fluid flowing through a luminal organ in vivo is to be obtained. $V_\theta(r, \theta) = w \cdot V^-_\theta + (1-w) \cdot V^+_\theta$ is calculated to obtain a calculated value $V_\theta(r, \theta)$ of the flow rate regarding a component of the fluid in the direction perpendicular to the ultrasonic beam direction. Here, the weight w is a value proportional to the distance d from the wall on one side of the organ at least when the distance is smaller than a predetermined distance from the wall on the one side, and the weight is a value proportional to the distance d' from the wall on the other side of the organ at least when the distance is smaller than a predetermined distance from the wall on the one other side.

2 Claims, 6 Drawing Sheets (51) Int. Cl.
 *A61B 8/08* (2006.01)
 *G01S 15/89* (2006.01)

(56) References Cited

U.S. PATENT DOCUMENTS

| | | | |
|---|---|---|---|
| 6,149,595 | A | 11/2000 | Seitz et al. |
| 2001/0016686 | A1* | 8/2001 | Okada ............... A61B 8/13 600/454 |
| 2004/0243006 | A1 | 12/2004 | Nakata et al. |
| 2005/0107705 | A1 | 5/2005 | Pedrizzetti et al. |
| 2009/0163816 | A1 | 6/2009 | Azuma et al. |
| 2011/0218435 | A1 | 9/2011 | Srinivasan et al. |

FOREIGN PATENT DOCUMENTS

| | | | |
|---|---|---|---|
| JP | 2005-102718 | A | 4/2005 |
| JP | 4698686 | B2 | 6/2011 |
| JP | 2012-5690 | A | 1/2012 |

OTHER PUBLICATIONS

Garcia et al., "Two-Dimensional Intraventricular Flow Mapping by Digital Processing Conventional Color-Doppler Echocardiography Images", Oct. 2010, pp. 1-10 1701-1712, vol. 29, No. 10, IEEE Transactions on Medical Imaging, IEEE.

Japan Patent Office, Office Action for Japanese Patent Application No. 2012-060973, Nov. 19, 2013.

International Preliminary Report on Patentability for PCT Application No. PCT/JP2012/076810, Jan. 8, 2013.

European Patent Office, Extended European Search Report for EP Patent Application No. 12871016.7, Nov. 12, 2015.

State Intellectual Property Office of the People's Republic of China, Office Action and Search Report for Chinese Patent Application No. CN201280071474.4, Nov. 2, 2015.

* cited by examiner

FLUID FLOW RATE DETECTION DEVICE

TECHNICAL FIELD

The present disclosure relates to a fluid flow rate detection device that detects a flow rate of fluid flowing through luminal organs in vivo such as a blood vessel, heart, etc.

BACKGROUND ART

Conventionally, for example, a method disclosed in Patent Document 1 is known as a method for detecting a flow rate of the blood flowing through a blood vessel, heart, etc., in vivo, on the basis of Doppler signals of the bloodstream detected from ultrasonic echo signals obtained by transmitting and receiving ultrasonic beams to and from a living organism. In the method disclosed in Patent Document 1, the bloodstream is divided into a base flow component and a vortex component for calculation.

Figure 5:
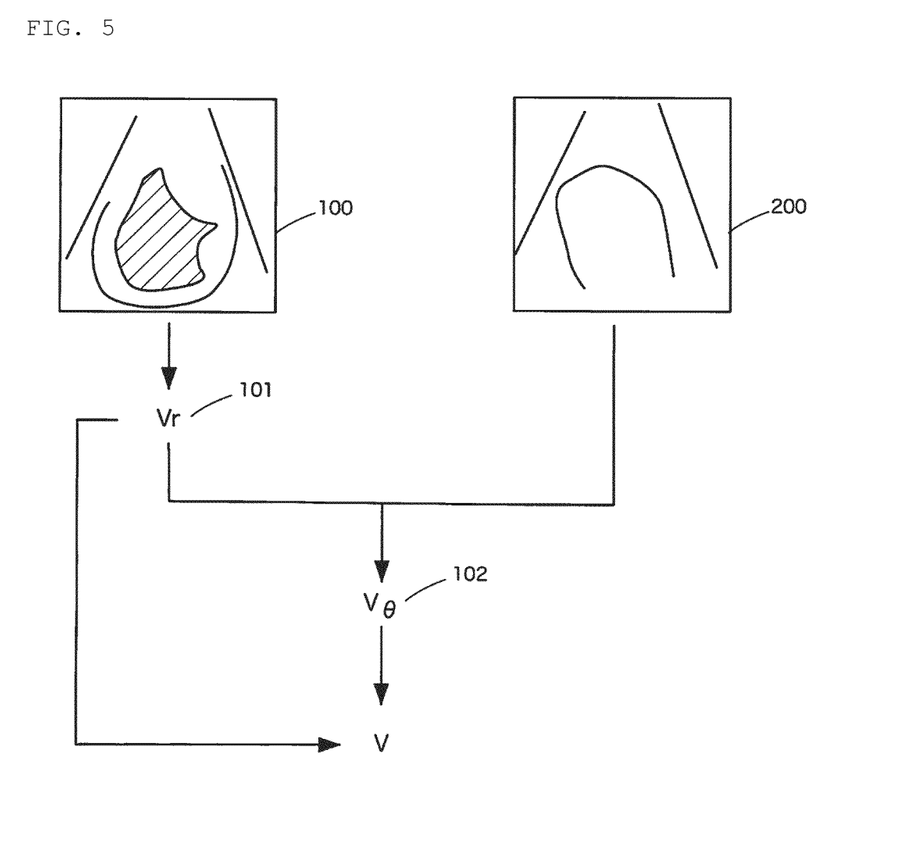
FIG. 5 is a schematic view showing an example of a conventional method for obtaining a blood flow rate.

On the other hand, Non-Patent Document 1 discloses a method for detecting a blood flow rate within the left ventricle (LV) in the heart. Specifically, this method discloses, as shown in FIG. 5, obtaining two-dimensional color Doppler images 100 and continuous B mode images 200 by a known ultrasonic diagnosis method, and then, obtaining information 101 regarding velocities (Radial Velocities) Vr in the ultrasonic beam direction on the basis of the two-dimensional color Doppler images 100, whereas detecting motion velocities of the left ventricle wall on the basis of the B mode images 200 by a widely known method such as spectrum tracking.

Then, information 102 regarding velocities $V_\theta$ in the angular direction perpendicular to the ultrasonic beam direction is obtained using the equation of continuity represented by Formula (1)

[Calculation Formula 1]

Formula (1)

$$\partial_\theta V_{74}(r,\theta) = -r\partial_r V_r(r,\theta) - V_r(r,\theta) \quad (1)$$

Here, $$\partial_x f(x,y) \quad \text{[Calculation Formula 2]}$$

is a simplified expression of $$\frac{\partial f(x,y)}{\partial x} \quad \text{[Calculation Formula 3]}$$

(the same is true in below).

Figure 6:
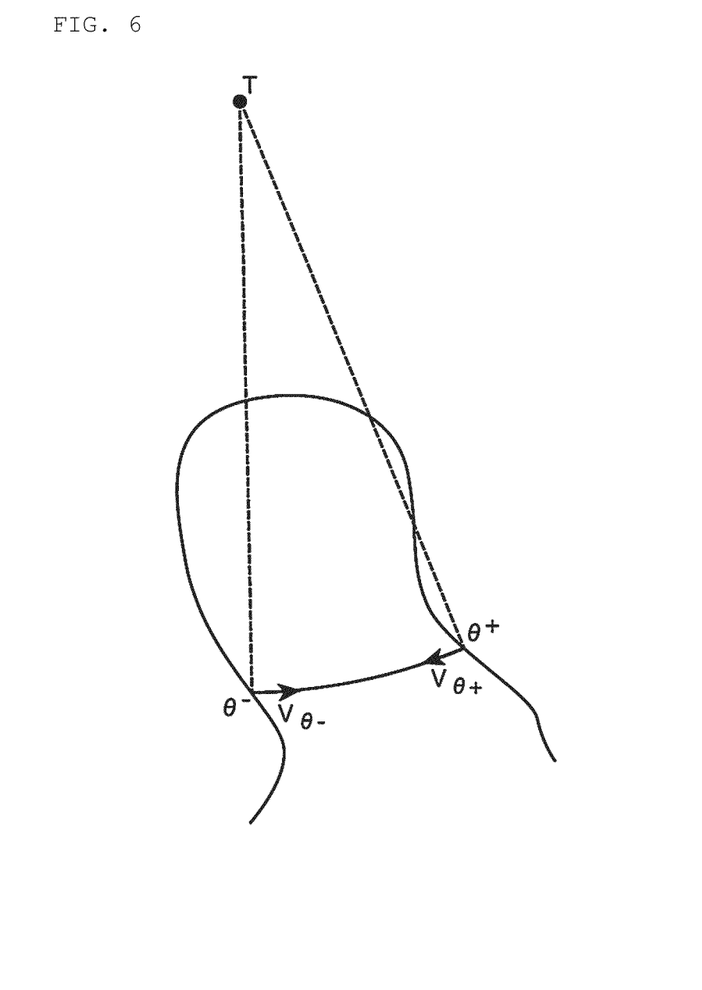
FIG. 6 is an explanatory view showing examples of motion velocities of the walls of an organ to be detected.

Specifically, as shown in FIG. 6, in the two-dimensional polar coordinate system $(r, \theta)$ with the origin at the ultrasonic beam source T, the motion velocity of the left ventricle wall on one side (for example, the posterior wall) at a radial position r is represented by $V_\theta^-(r)$, and the motion velocity of the left ventricle wall on the other side (for example, the anterior wall) at the radial position r is represented by $V_\theta^+(r)$.

Here, the velocity $V_\theta$ at a point with a radial position r and an angular position $\theta$ (hereinafter referred as a position of interest), in the angular direction perpendicular to the ultrasonic beam direction, may be obtained by integrating Formula (1). The results of the integral according to Formula (1) are a first integral result obtained upon integration from the posterior wall side, and a second integral result obtained upon integration from the anterior wall side. Namely, the first integration can be represented by Formula (2) wherein integration is performed from the position $\theta-$ on the posterior wall to the position of interest $\theta$ along a line having a constant radial position r (in the angular direction), using the motion velocity $V_\theta^-(r)$ of the posterior wall as the integral constant.

[Calculation Formula 4]

Formula (2)

$$V_\theta^-(r,\theta) = V_{\theta-}(r) + \int_{\theta-}^{\theta} \partial_\theta V_\theta(r,\theta) d\theta \quad (2)$$

The second integration can be represented by Formula (3) wherein integration is performed from the position $\theta^+$ on the anterior wall to the position of interest $\theta$ along the line having the constant radial position r (in the angular direction), using the motion velocity $V_\theta^+(r)$ of the anterior wall as the integral constant.

[Calculation Formula 5]

Formula (3)

$$V_\theta^+(r,\theta) = V_{\theta+}(r) - \int_{\theta}^{\theta+} \partial_\theta V_\theta(r,\theta) d\theta \quad (3)$$

As it turns out, two boundary conditions, namely, the condition for the posterior wall side and the condition for the anterior wall side, can be set for a first-order partial differential equation, and as a result, an extra solution is obtained. Accordingly, these solutions are subjected to weighted averaging to reduce error. The velocities $V_\theta$ at the position of interest $(r, \theta)$, in the angular direction perpendicular to the ultrasonic beam direction, namely, first integral result and the second integral result are subjected to weighted averaging with a weight w, as shown in Formula (4).

[Calculation Formula 6]

Formula (4)

$$V_\theta(r,\theta) = wV_\theta^-(r,\theta) + (1-w)V_\theta^+(r,\theta) \quad (4)$$
$$= [wV_{\theta-}(r) + (1-w)V_{\theta+}(r)] +$$
$$\left[ w\int_{\theta-}^{\theta} \partial_\theta V_\theta(r,\theta) d\theta + (1-w)\int_{\theta}^{\theta+} \partial_\theta V_\theta(r,\theta) d\theta \right]$$

Here, w represents a weight, and on the basis of the technical common sense, the weight is selected so that the solutions $V_\theta$ of Formula (2) and Formula (3) are to be the same. Specifically, the weight is determined as a function of r and $\theta$ representing a position along an integral path, as shown in Formula (5).

[Calculation Formula 7]

Formula (5)

$$w(r,\theta) = 1 - \frac{\int_{\theta-}^{\theta} [\partial_\theta V_\theta(r,\theta) - \partial_\theta V_\theta(r,\theta^-)] d\theta}{\int_{\theta-}^{\theta+} [\partial_\theta V_\theta(r,\theta) - \partial_\theta V_\theta(r,\theta^-)] d\theta} \quad (5)$$
$$= \frac{\int_{\theta}^{\theta+} [\partial_\theta V_\theta(r,\theta) - \partial_\theta V_\theta(r,\theta^+)] d\theta}{\int_{\theta-}^{\theta+} [\partial_\theta V_\theta(r,\theta) - \partial_\theta V_\theta(r,\theta^+)] d\theta}$$

In addition, when the denominator in Formula (5) becomes closer to "0" and diverged, Formula (5) can be replaced by an approximate Formula (6), wherein $\partial_\theta V_\theta$ can be obtained by Formula (1).

[Calculation Formula 8]

Formula (6)

$$w(r,\theta) = 1 - \frac{\int_{\theta^-}^{\theta}[\partial_\theta V_\theta(r,\theta) - \min(\partial_\theta V_\theta)(r)]d\theta}{\int_{\theta^-}^{\theta^+}[\partial_\theta V_\theta(r,\theta) - \min(\partial_\theta V_\theta)(r)]d\theta} \quad (6)$$

$$= \frac{\int_{\theta}^{\theta^+}[\partial_\theta V_\theta(r,\theta) - \min(\partial_\theta V_\theta)(r)]d\theta}{\int_{\theta^-}^{\theta^+}[\partial_\theta V_\theta(r,\theta) - \min(\partial_\theta V_\theta)(r)]d\theta}$$

RELATED ARTS

Patent Document

Patent Document 1: Japanese Patent No. 4698686

Non-Patent Document

Non-Patent Document 1: Damien Garcia, et al., "Two-Dimensional Intraventricular Flow Mapping by Digital Processing Conventional Color-Doppler Echocardiography Images", IEEE Transactions on Medical Imaging, Vol. 29, No. 10, October 2010, 1701-1712

However, the technology disclosed in Non-Patent Document 1 has drawbacks that unreasonable results may be obtained such that when $V_\theta(r, \theta+)$ is used in Formula (5) or Formula (6), the weight at the $\theta^-$ side wall is calculated to be too large or too small, resulting in enlarging the velocity component of the fluid in the direction perpendicular to the moving direction of the wall, or enlarging the velocity of the fluid away from the wall to be larger than the motion velocity of the wall, and accordingly, the calculation results may have low adequacy from the medical point of view.

The present disclosure has been made in view of the above drawbacks, and an object of the present disclosure is to provide a fluid flow rate detection device which can be evaluated as adequate from the medical point of view.

SUMMARY

In order to solve the drawbacks of the prior arts, the present disclosure provides a fluid flow rate detection device comprising: an ultrasonic probe which repeats operations to transmit/receive ultrasonic beams at a plurality of angular direction positions to/from a fluid flowing through a luminal organ in vivo, and to output an echo data array with respect to each ultrasonic beam; a first calculation portion which calculates the flow rate regarding the ultrasonic beam direction component of the fluid, on the basis of the echo data array; a detection portion which obtains B mode images of the luminal organ at a plurality of time points on the basis of the repeatedly obtained echo data arrays, and on the basis of the B mode images at the plurality of time points, detects motion velocities of the wall on one side and the wall on the other side of the luminal organ at a plurality of angular directions; and a second calculation portion which obtains a first integral result $V_\theta^-$ as a calculated value of a flow rate regarding a component of the fluid in the direction perpendicular to the ultrasonic beam direction, the first integral result being obtained by integrating the equation of continuity relating to flow rate information regarding a component of the fluid in the direction perpendicular to the ultrasonic beam direction and flow rate information regarding a component of the fluid in the ultrasonic beam direction, from one side of the liminal organ to a position of interest (r, θ) at which a flow rate is to be obtained, using the motion velocity of the wall on the one side detected by the detection portion as a boundary condition for integration, obtains a second integral result $V_\theta^+$ as a calculated value of a flow rate regarding a component of the fluid in the direction perpendicular to the ultrasonic beam direction, the second integral result being obtained by integrating the equation of continuity relating to the flow rate information regarding the component of the fluid in the direction perpendicular to the ultrasonic beam direction and the flow rate information regarding the component of the fluid in the ultrasonic beam direction, from the other side of the liminal organ to the position of interest (r, θ) at which a flow rate is to be obtained, using the motion velocity of the wall of the other side detected by the detection portion as a boundary condition for integration, calculates $V_\theta(r, \theta) = w \cdot V_\theta^- + (1-w) \cdot V_\theta^+$ using the first integral result $V_\theta^-$, the second integral result $V_\theta^+$, and the weight w, to obtain a calculated value $V_\theta(r, \theta)$ as a flow rate regarding the component of the fluid in the direction perpendicular to the ultrasonic beam direction; wherein the weight w is proportional to a distance d from the wall on the one side, at least until a predetermined distance from the wall on the one side, and is proportional to a distance d' from the wall on the other side until a predetermined distance from the wall on the other side.

According to the present disclosure, adequate results from the medical point of view will be obtained.

EMBODIMENT

An embodiment of the present disclosure will be explained with reference to the drawings. As exemplified in FIG. 1, a fluid flow rate detection device according to an embodiment of the present disclosure comprises an ultrasonic probe 1, a transmission/reception unit 2, a transmission/reception control unit 3, a calculation unit 4, and a display unit 5. Here, the calculation unit 4 comprises a tomographic image producing unit 41, a color Doppler calculation unit 42, a wall motion velocity calculation unit 43, a velocity vector calculation unit 44, a weight setting unit 34, and a display image producing unit 45. Each of these units may be realized as software by a program control device such as a CPU, etc. In this case, the program control device is operated in accordance with a program stored in a non-transitory computer readable storage medium such as a storage unit, to thereby realize the configuration of the respective units mentioned above as software.

Figure 1:
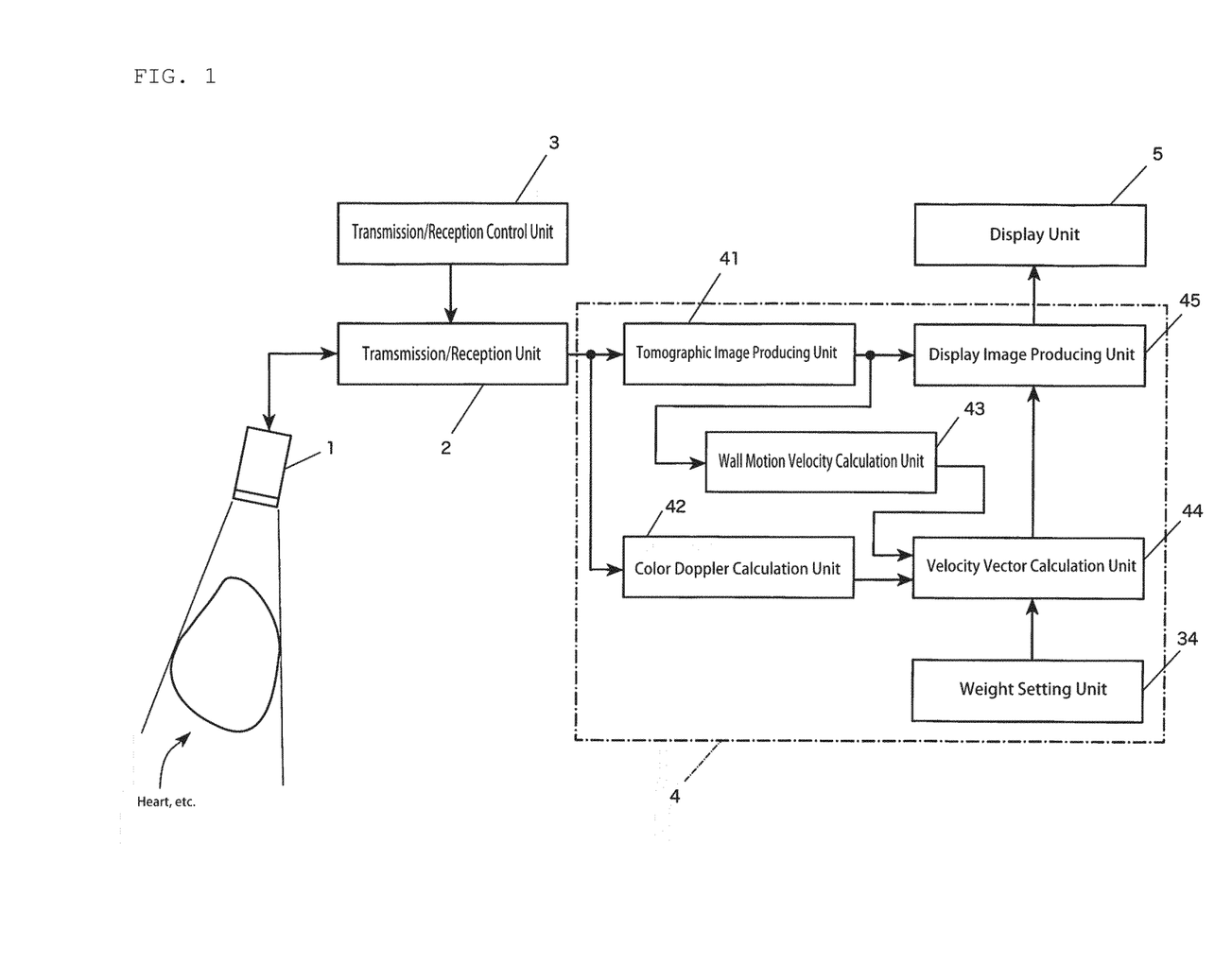
FIG. 1 is a block diagram showing a configuration example of a fluid flow rate detection device according to an embodiment of the present disclosure.

The ultrasonic probe 1 is, for example, a sector scan type probe or a convex scan type probe. The transmission/reception unit 2 is controlled by the transmission/reception control unit 3, and transmits/receives ultrasonic beams E at a plurality of angular direction positions, with the ultrasonic probe 1 at the body surface side, to/from a fluid flowing through, for example, a blood vessel, the heart, etc., i.e., a luminal organ which is located within a living body, such as a human body, and the like, and which contains a fluid to be measured thereinside (hereinafter, referred to as a luminal organ to be detected).

Figure 2:
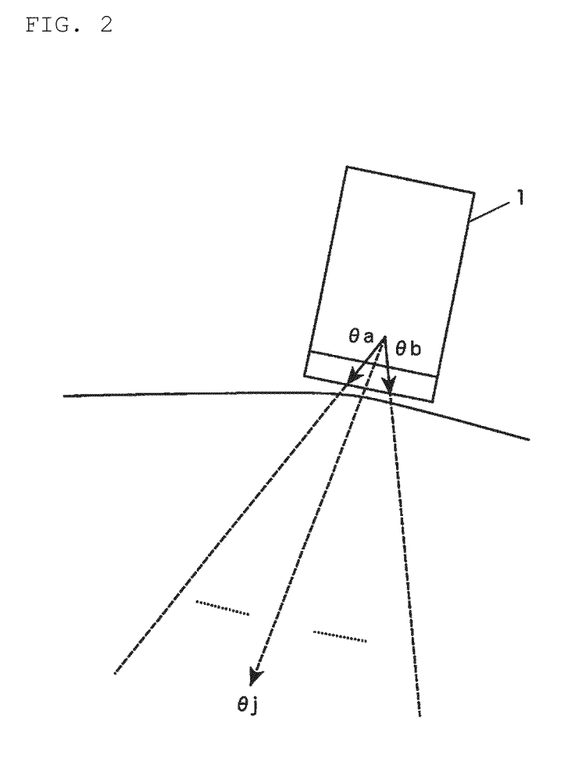
FIG. 2 is an explanatory view showing examples of ultrasonic beam transmission/reception directions by a fluid flow rate detection device according to an embodiment of the present disclosure.

In response to the operation by the transmission/reception control unit 3, as exemplified in FIG. 2, ultrasonic beams $E(\theta j)$ (j=1, 2, . . . , n) are respectively transmitted in a plurality of angular directions $\theta 1, \theta 2, \ldots, \theta n$ ($\theta a \leq \theta 1 \leq \theta 2 < \ldots < \theta n \leq \theta b$) determined in advance in a predetermined angle range ($\theta a < \theta < \theta b$) on a virtual plane (observation plane), with the origin set at a virtually located point on side of the ultrasonic probe 1 when viewed from the body surface. The transmitted ultrasonic beams are reflected by organs in the body or the composition of fluids (in case of blood, for example, erythrocyte), and are returned to the ultrasonic probe 1. The transmission/reception unit 2 acquires, through the ultrasonic probe 1, ultrasonic reception signal data (echo data) $ei(\theta j)=\{(\theta j, t1), (\theta j, t2), \ldots, (\theta j, tm)\}$ (j1, 2, . . . , n, and {*} represents a data array of *) reaching for a plurality of times at a predetermined time interval, and obtains an echo data array for each ultrasonic beam. Then, the transmission/reception unit 2 outputs the echo data array for each ultrasonic beam to the tomographic image producing unit 41 and the color Doppler calculation unit 42 of the calculation unit 4. The transmission/reception control unit 3 controls the transmission/reception unit 2 such that the above operations are repeated at a predetermined time interval. The transmission/reception unit 2 outputs the echo data array $ei(\theta 1) \ldots ei(\theta n)$ (i=1, 2, acquired at the i-th repeat.

In the present embodiment, the tomographic image producing unit 41 produces a B mode image on the basis of the echo data arrays output from the transmission/reception unit 2. The color Doppler calculation unit 42 calculates a flow rate regarding the ultrasonic beam direction component of the fluid on the basis of the echo data arrays output from the transmission/reception unit 2, and produces a two-dimensional color Doppler image. The wall motion velocity calculation unit 43 accepts the B mode images of the luminal organ to be detected which have been produced at a plurality of time points, from the tomographic image producing unit, and on the basis of the B mode images produced at the plurality of time points, the wall motion velocity calculation unit 43 detects motion velocities of the wall on the one side and the wall on the other side of the luminal organ to be detected.

The velocity vector calculation unit 44 obtains a first integral result of a calculated value $V^-_\theta$ as a flow rate regarding a component of the fluid in the direction perpendicular to the ultrasonic beam direction, the first integral result being obtained by integrating the equation of continuity relating to flow rate information regarding a component of the fluid in the direction perpendicular to the ultrasonic beam direction and flow rate information regarding a component of the fluid in the ultrasonic beam direction, from one side of the liminal organ to be detected to a position of interest (r, $\theta$) at which a flow rate is to be obtained, using the prior detected motion velocity of the wall on the one side as a boundary condition for integration, and obtains a second integral result of a calculated value $V^+_\theta$ as a flow rate regarding a component of the fluid in the direction perpendicular to the ultrasonic beam direction, the second integral result being obtained by integrating the equation of continuity relating to the flow rate information regarding the component of the fluid in the direction perpendicular to the ultrasonic beam direction and the flow rate information regarding the component of the fluid in the ultrasonic beam direction, from the other side of the liminal organ to the position of interest (r, $\theta$) at which a flow rate is to be obtained, using the motion velocity of the wall on the other side detected by the detection portion as a boundary condition for integration.

The velocity vector calculation unit 44 calculates $$V_\theta(r,\theta) = w \cdot V^-_\theta + (1-w) \cdot V^+_\theta$$

using the first integral result $V^-_\theta$, the second integral result $V^+_\theta$, and the weight w, and obtains and outputs a calculated value $V_\theta(r, \theta)$ as a flow rate regarding the component of the fluid in the direction perpendicular to the ultrasonic beam direction.

Hereinbelow, operations of each unit of the calculation unit 4 will be specifically explained.

The tomographic image producing unit 41 produces a B mode image, using echo data arrays $ei(\theta 1) \ldots ei(\theta n)$ (i=1, 2, . . . ) output from the transmission/reception unit.

The color Doppler calculation unit 42 produces a two-dimensional color Doppler image using a p-th echo data arrays $ep(\theta 1) \ldots ep(\theta n)$ selected from among the echo data arrays $ei(\theta 1) \ldots ei(\theta n)$ (i=1, 2, . . . ), using previously determined conditions. Then, on the basis of the two-dimensional color Doppler image, the color Doppler calculation unit 42 calculates a flow rate Vr(r, $\theta$) (Radial Velocities) regarding a ultrasonic beam direction component (r-component) of the fluid, at a coordinate (r, $\theta$) in the luminal organ to be detected. The method for this calculation is widely known, and thus, an explanation therefor is omitted here. The selecting conditions may be selecting an echo data array when p=1, or when a time period T has passed from the start of the measurement.

On the basis of the B mode image which has been produced, the wall motion velocity calculation unit 43 detects a $\theta$-axis direction component $V_{\theta-}(r)$ of a motion velocity of the wall surface at a position (r, $\theta^-$) using the speckle tracking method, etc., the $\theta$-axis direction being perpendicular to the ultrasonic beam direction, and the position (r, $\theta^-$) being a position on the wall surface which is located on the one side of the luminal organ to be detected and is in contact with the fluid, at a distance r from the ultrasonic probe 1 (radiation source of the ultrasonic waves).

Further, on the basis of the B mode image which has been produced, the wall motion velocity calculation unit 43 detects a $\theta$-axis direction component $V_\theta^+(r)$ of a motion velocity of the wall surface at a position (r, $\theta^+$) using the same method, the $\theta$-axis direction being perpendicular to the ultrasonic beam direction, and the position (r, $\theta^-$) being a position on the wall surface which is located on the other side of the luminal organ to be detected and is in contact with the fluid, at a distance r from the ultrasonic probe 1 (radiation source of the ultrasonic waves).

The B mode image to be processed by the wall motion velocity calculation unit 43 is drawn on the XY orthogonal coordinate system. Accordingly, the motion velocity of the wall of the luminal organ to be detected, obtained by speckle tracking, etc., is a value according to the XY orthogonal coordinate system. The wall motion velocity calculation unit 43 transforms this value according to the XY orthogonal coordinate system to a value according the polar coordinate system (r, $\theta$) with the origin at the position of the ultrasonic probe 1 (radiation source of ultrasonic waves), and outputs the transformed value.

The velocity vector calculation unit 44 obtains a fluid velocity $V_\theta$ in the angular direction perpendicular to the ultrasonic beam direction, by the equation of continuity represented by Formula (1) which uses the two-dimensional color Doppler image (blood flow rate information Vr(r, θ) in the ultrasonic beam direction) output from the color Doppler calculation unit 42, and $V_\theta^-(r)$ and $V_\theta^+(r)$ output from the wall motion velocity calculation unit 43.

[Calculation Formula 1]

$$\partial_\theta V_{T4}(r,\theta) = -r\partial_r V_r(r,\theta) - V_r(r,\theta) \quad (1)$$

Here, $$\partial_x f(x,y) \quad \text{[Calculation Formula 2]}$$

is a simplified expression of $$\frac{\partial f(x,y)}{\partial x} \quad \text{[Calculation Formula 3]}$$

(the same is true in below).

At this time, the velocity $V_\theta$ in the angular direction perpendicular to the ultrasonic beam direction, at a point with a radial position r and an angular position θ (hereinafter, referred to as a position of interest) can be obtained by integrating Formula (1). The results of this integration are a first integral result obtained by integrating from the position $\theta^-(r)$ located on the wall on the one side of the luminal organ to be detected, and a second integral result obtained by integrating from the position $\theta^+(r)$ located on the wall on the other side of the luminal organ to be detected. Namely, the first integration is performed by integrating from the position $\theta^-(r)$ on the wall on the one side along a line having a constant radius r (in the angular direction) to the position of interest θ(r), using the motion velocity $V_\theta^-(r)$ of the wall on the one side as an integral constant. The first integration can be represented by Formula (2).

[Calculation Formula 4]

$$V_\theta^-(r,\theta) = V_{\theta-}(r) + \int_{\theta-}^{\theta} \partial_\theta V_\theta(r,\theta) d\theta \quad (2)$$

Whereas, the second integration is performed by integrating from the position $\theta^+(r)$ on the wall on the other side along a line having a constant radius r (in the angular direction) to the position of interest θ(r), using the motion velocity $V_\theta^-(r)$ of the wall on the other side (such as the anterior wall) as an integral constant. The second integration can be represented by Formula (3).

[Calculation Formula 5]

$$V_\theta^+(r,\theta) = V_{\theta+}(r) - \int_{\theta-}^{\theta+} \partial_\theta V_\theta(r,\theta) d\theta \quad (3)$$

The velocity vector calculation unit 44 calculates the integrations represented by Formula (2) and (3), with respect to each of a plurality of predetermined radial positions r1, r2, and so on, to obtain first and second integral results $V^-_\theta(r1)$, $V^+_\theta(r1)$, $V^-_\theta(r2)$, $V^+_\theta(r2)$, and so on, for respective radial positions.

After all, this potion that the boundary conditions can be set for the wall on the one side and the wall on the other side, and thus, in total, two boundary conditions can be set for the first-order partial differential equation. As a result, an extra solution is obtained. Therefore, these solutions are subjected to weighted averaging to reduce error. In other words, the velocity vector calculation unit 44 performs weighted averaging of the first integral result $V^-_\theta(r)$ and the second integral result $V^+_\theta(r)$ (wherein, r=r1, r2 ...), with the weight w output from the weight setting unit 34, and calculates Formula (4) to obtain the velocity $V_\theta(r, \theta)$ in the angular direction perpendicular to the ultrasonic beam direction, at the position of interest (r, θ).

[Calculation Formula 6]

$$\begin{aligned} V_\theta(r,\theta) &= wV_\theta^-(r,\theta) + (1-w)V_\theta^+(r,\theta) \\ &= [wV_{\theta-}(r) + (1-w)V_{\theta+}(r)] + \\ &\quad \left[w\int_{\theta-}^{\theta} \partial_\theta V_\theta(r,\theta)d\theta + (1-w)\int_{\theta}^{\theta+} \partial_\theta V_\theta(r,\theta)d\theta\right] \end{aligned} \quad (4)$$

Thereby, the velocity vector calculation unit 44 obtains the fluid flow rate at the position (r, θ) in the luminal organ to be detected, while the flow rate is resolved into the component Vr(r, θ) in the ultrasonic beam direction and the component $V_\theta(r, \theta)$ in the direction perpendicular to the ultrasonic beam direction.

The weight setting unit 34 sets the weight so that the weight is proportional to the distance d from the wall on the one side at least until the distance d reaches a predetermined distance from the wall on the one side, and that the weight is proportional to the distance d' from the wall on the other side until the distance d' reaches a predetermined distance from the wall on the other side. As an example, the weight setting unit 34 according to an embodiment sets the weight w as follows. First, regarding the radial direction coordinate ri (ri represents any one of r1, r2, and so on), the distance D(ri) on the integral path (the path with a constant radial direction coordinate r) from the wall on the one side to the wall on the other side of the luminal organ to be detected can be obtained by D(ri)=ri·|θ⁺(ri)−θ⁻(ri)| (|*| represents calculating an absolute value of *). Also, the distance d from the wall on the one side to the position of interest (ri, θ), can be obtained by d=ri·|θ−θ⁻(ri)|. Here, the weight setting unit 34 sets the weight w as w=d/D(ri)=|θ−θ⁻(ri)|/|θ⁺(ri)−θ⁻(ri)|. The weight set accordingly is a value which is linear to the angular direction coordinate θ of the position of interest (proportional to the distance d). This proportional relationship can be satisfied regardless of the radial direction position r. In addition, when the weight w is set to be proportional to the distance d from the wall on the one side, naturally, w=d/D(ri)=(D(ri)−r')/(ri) (wherein, r' represents a distance on the integral path from the wall on the other side to the position of interest) is satisfied, and thus, the weight w is proportional to the distance d' from the wall on the other side.

This weight does not function to make the first and second integral results identical at each point on the integral path, unlike the weight set by Formula (5) or Formula (6). However, by setting such a weight which appears to go against the technical common sense, the fluid flow rates near opposite walls are revealed to naturally reflect the motion velocities of the walls.

The display image producing unit 45 combines an image representing a velocity vector calculated by the velocity vector calculation unit 44 with respect to each point with a coordinate (r, θ), on the B mode image output from the tomographic image producing unit 41, to produce and output an image to be displayed.

The fluid flow rate detection device according to the present embodiment has a structure as mentioned above, and is operated as below. Specifically, in the following example, the blood flow rate within the left ventricle (LV) of the heart is to be detected. In this example, the ultrasonic probe 1 transmits ultrasonic beams E at a plurality of angular direction positions, from the body surface side toward the blood flowing through the left ventricle of the heart within a living body such as a human body. Then, the ultrasonic probe 1 outputs echo data arrays e(θ1)...e(θn) obtained respectively for the transmitted ultrasonic beams, to the calculation unit 4 through the transmission/reception unit 2. The ultrasonic probe 1 repeats these operations at each predetermined time (for example, at a time interval of $\Delta t$). The echo data arrays at the k-th repeat are represented as $ek(\theta 1) \ldots ek(\theta n)$ (k=1, 2, ...).

Figure 3:
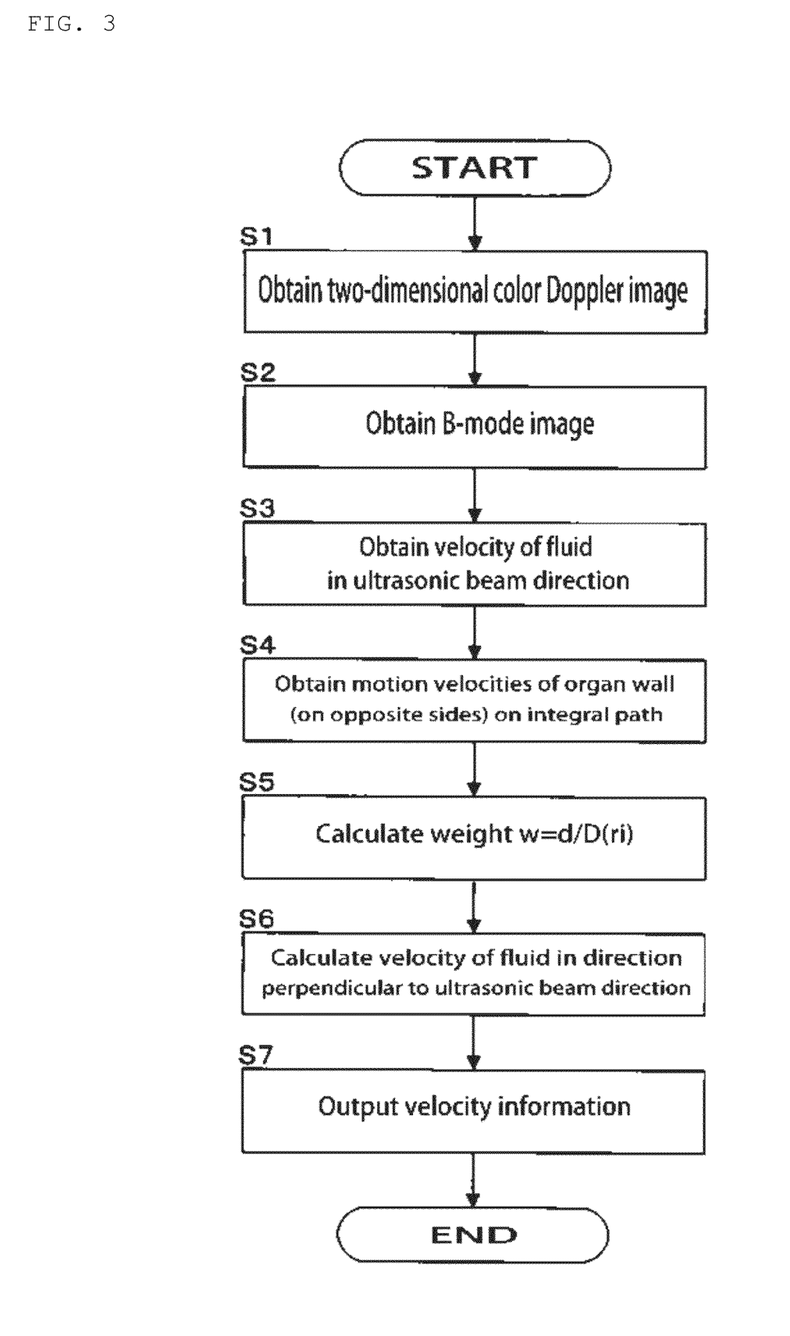
FIG. 3 is a flowchart showing an operation example of a fluid flow rate detection device according to an embodiment of the present disclosure.

As exemplified in FIG. 3, the velocity vector calculation unit 44 obtains a two-dimensional color Doppler image calculated on the basis of the p-th echo data arrays $ep(\theta 1) \ldots ep(\theta n)$ selected under predetermined conditions from among the echo data arrays $ek(\theta 1) \ldots ek(\theta n)$ (k=1, 2, output from the ultrasonic probe 1 (S1). The wall motion velocity calculation unit 43 obtains a plurality of B mode images from the echo data arrays output from the ultrasonic probe 1 (S2). Then, the wall motion velocity calculation unit 43 obtains blood velocities in the ultrasonic beam direction (Radial Velocities) $Vr(ri, \theta j)$, at a plurality of predetermined points (referred to as specified points) $(ri, \theta j)$ (wherein, i=1, 2, ..., j=1, 2 ...) on the basis of the two-dimensional color Doppler image (S3).

On the other hand, on the basis of the plurality of B mode images obtained in Step 2, the wall motion velocity calculation unit 43 obtains a position $\theta^-(ri)$ on the posterior wall and a position $\theta^+(ri)$ on the anterior wall of the left ventricle which is a luminal organ to be detected, when r=ri(i=1, 2, ... ), using a widely known method such as speckle tracking, etc. At this time, these positions are obtained by transforming the position information obtained as X-Y coordinates of the image by the speckle tracking method, etc., to polar coordinates with the origin at the position of the ultrasonic probe 1 which is a source of ultrasonic waves.

The wall motion velocity calculation unit 43 uses the position information on each wall, and information regarding the time when each of the plurality of B mode images is obtained (for example, the time interval $\Delta t$), to thereby obtain a motion velocity $V_\theta^-(ri)$ of the wall on the one side (for example, the posterior wall) of the left ventricle, and a motion velocity $V_\theta^+(ri)$ of the wall of the other side (for example, the anterior wall) of the left ventricle, with respect to each radial position ri (i=1, 2, ... ) (S4).

The weight setting unit 34 obtains the position $\theta^-(ri)$ on the one end (posterior wall side) and the position $\theta^+(ri)$ on the other end (anterior wall side) regarding the integral path according to Formula (1), at each radial direction position r=ri(i=1, 2, ... ) having a specified point. Then, the weight setting unit 34 calculates the weight $w=d/D(ri)=|\theta(ri)-\theta^-(ri)|/|\theta^+(ri)-\theta^-(ri)|$ at the specified points $(ri, \theta j)$ (j=1, 2, ... ) on the integral path, using the distance $d=ri\cdot|\theta(ri)-\theta^-(ri)|$ from the one end and the entire length of the integral path $D=ri\cdot|\theta^+(ri)-\theta^-(ri)|$ (S5).

The velocity vector calculation unit 44 calculates Formula (4) using the weight w, and obtains the blood velocity $V_\theta(ri, \theta j)$ in the angular direction perpendicular to the ultrasonic beam direction, at each specified point $(ri, \theta j)$ (i=1, 2, ..., j=1, 2 ...) (S6)

Accordingly, the blood velocity V at each specified point $(ri, \theta j)$ (i=1, 2, ..., j=1, 2 ...) is obtained while the velocity V is resolved into the velocity component $Vr(ri, \theta j)$ in the ultrasonic beam direction and the velocity component $V_\theta(ri, \theta j)$ in the angular direction perpendicular to the ultrasonic beam direction. The velocity vector calculation unit 44 outputs the value of the velocity V obtained at each specified point (S7).

The velocity vector calculation unit 44 repeats the above-mentioned processes while, for example, incrementing a predetermined value in Step S1, namely, p=1, 2, .... Therefore, on the basis of the echo data arrays $ek(\theta 1) \ldots ek(\theta n)$ (k=1, 2, obtained at each repeat, B mode images and blood velocities V at the time points when respective echo data arrays are obtained, can be obtained. The velocity vector calculation unit 44 may draw an arrow having a length and a direction of the velocity vector $Vk(ri, \theta j)$ obtained for each specified point on the basis of the k-th echo data arrays, with the base of the arrow at the position of each specified point $(ri, \theta j)$ on the B mode image obtained on the basis of the k-th echo data arrays. To this end, the display image producing unit 45 of the calculation unit 4 combines the images expressing the velocity vectors at respective points having the coordinate $(r, \theta)$ calculated by the velocity vector calculation unit 44, onto the B mode image output from the B mode image, to produce and output an image for display. Namely, the display image producing unit 45 calculates a position (position on the XY coordinate system) $P(x, y)$ corresponding to each specified point on the B mode image output from the tomographic image producing unit 41, and transforms the velocity vector $Vk(ri, \theta j)$ into each component (X-axis direction component and Y-axis direction component) in the XY coordinate system, that is, values $Vk\_x(x, y)$ (X-axis direction component) and $Vk\_y(x, y)$ (Y-axis direction component). Then, the display image producing unit 45 multiplies a predetermined coefficient $\alpha$ (zoom ratio) to obtain a position $(\alpha\cdot Vk\_x(x, y), \alpha Vk\_y(x, y))$, and draws an arrow from the specified point at $(x, y)$ to the thus obtained position $(\alpha V\cdot Vk\_x(x, y), \alpha\cdot Vk\_y(x, y))$.

When this drawing is repeated with respect to each image and value obtained on the basis of the echo data arrays $ek(\theta 1) \ldots ek(\theta n)$ (k=1, 2, obtained upon each repeat, the bloodstream within the heart is drawn together with the movement of the heart, using each image as an frame of animation. The display image producing unit 45 may display an animation while continuously replacing the image of each frame, or may display by arranging the images of the frames in matrix.

Figure 4:
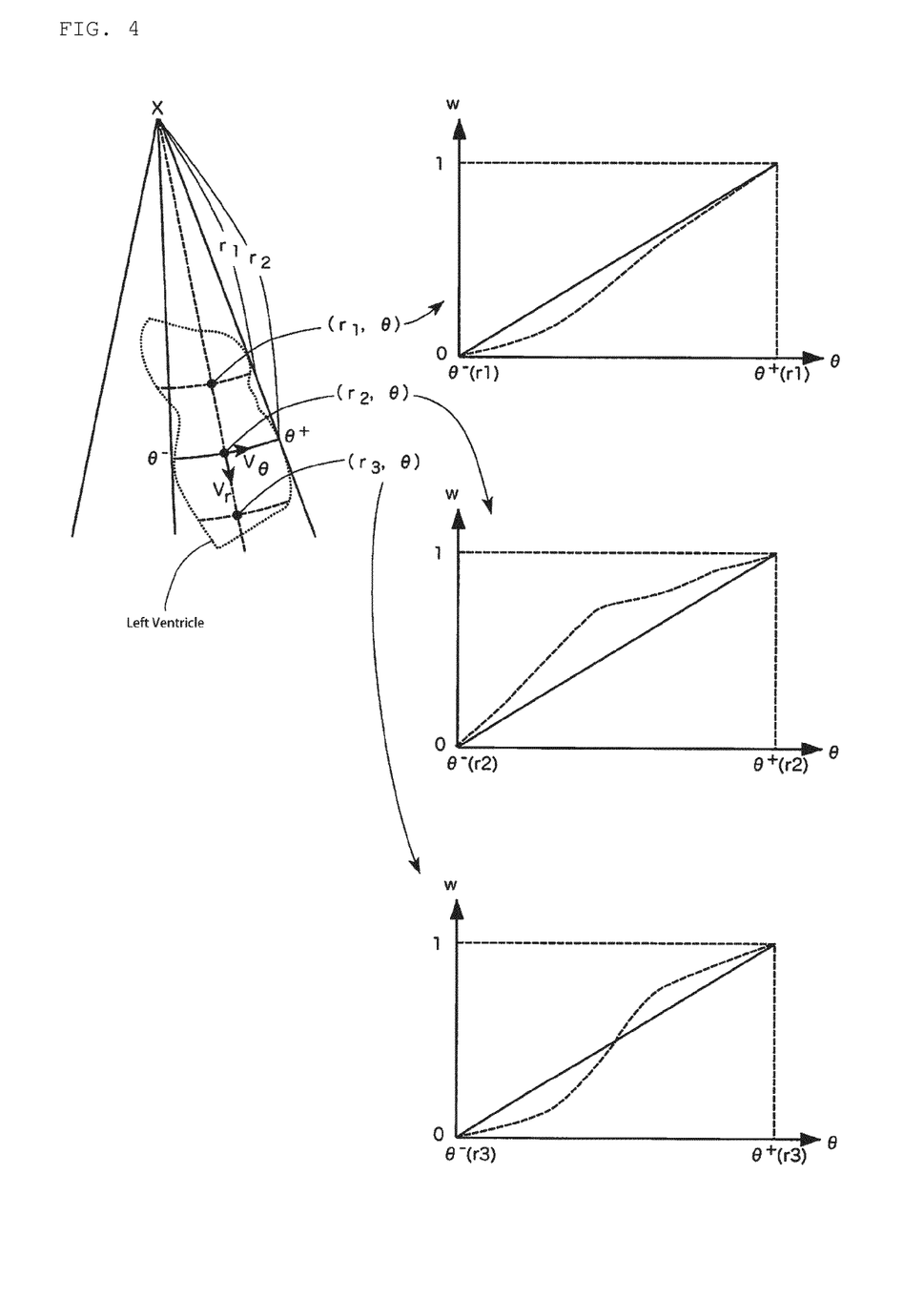
FIG. 4 is an explanatory view showing an example of the weight to be used by a fluid flow rate detection device according to an embodiment of the present disclosure.

With respect to the weight to be used for calculating Formula (4), FIG. 4 shows a comparison between an example using the conventional weight, and an example using the weight according to the present embodiment. As shown in FIG. 4, the conventional weight (shown by the dotted line in FIG. 4) varies depending on the radial direction positions (shown by r1, r2, r3 in FIG. 4), and further, the conventional weight does not always change in proportion to the ratio of the distance from the wall relative to the entire length of the integral path, even near the wall in the angular direction. Whereas, the weight according to the present disclosure (shown by the solid line in FIG. 4) changes in proportion to the ratio of the distance from the wall relative to the entire length of the integral path, at least near the wall, regardless of the radial direction position at least within a predetermined range from each wall (predetermined range from opposite ends of the integration range).

The weight according to the present embodiment is not usually adopted from the viewpoint of the technical common sense, because the use of this weight does not match the integral result from the wall on the one side and the integral result from the wall on the other side, at each point on the integral path. However, in the present embodiment, this weight is intentionally adopted. It has been found that the detection result obtained with the use of this weight according to the present embodiment can be evaluated as adequate from the medical point of view.

In the present embodiment, as far as the weight is calculated by $w=d/D(ri)=|\theta(ri)-\theta^-(ri)|/|\theta^+(ri)-\theta^-(ri)|$ until the predetermined distance 1 from each wall, the weight does not have to satisfy the above formula at a position with a distance larger than the distance 1 from the wall. For example, at the position where both $r|-\theta^+|$ and $r|\theta-\theta^-|$ are larger than the predetermined distance 1, the weight may be represented by Formula (5) (or Formula (6) similar thereto), whereas, at the position where either $r|\theta-\theta^+|$ or $r|\theta-\theta^-|$ is smaller than the predetermined distance 1, the weight may be represented by $w=d/D(ri)=|\theta(ri)-\theta^-(ri)|/|\theta^+(ri)-\theta^-(ri)|$. Namely, the weight can be represented as follows.

[Calculation Formula 9]

$$w(r,\theta) = 1 - \frac{\int_{\theta^-}^{\theta}[\partial_\theta V_\theta(r,\theta) - \partial_\theta V_\theta(r,\theta^-)]d\theta}{\int_{\theta^-}^{\theta^+}[\partial_\theta V_\theta(r,\theta) - \partial_\theta V_\theta(r,\theta^-)]d\theta} \quad (r|\theta-\theta^+|>l,\, r|\theta-\theta^-|>l)$$

$$w(r,\theta) = \frac{|\theta-\theta^-|}{|\theta^- - \theta^+|} \quad (r|\theta-\theta^+|\le l \text{ or } r|\theta-\theta^-|\le l)$$

In addition, at the position where both $r|\theta-\theta^+|$ and $r|\theta-\theta^-|$ are larger than the predetermined distance 1, the weight does not have to be represented by Formula (5) or (6), but can be represented by a monotonically decreasing function experimentally defined with respect to $|\theta-\theta^-|$.

EXPLANATION ON NUMERALS

1 ultrasonic probe, 2 transmission/reception unit, 3 transmission/reception control unit, 4 calculation unit, 5 display unit, 34 weight setting unit, 41 tomographic image producing unit, 42 color Doppler calculation unit, 43 wall motion velocity calculation unit, 44 velocity vector calculation unit, 45 display image producing unit

The invention claimed is:

1. A fluid flow rate detection device comprising:
an ultrasonic probe which repeats operations to transmit/receive ultrasonic beams at a plurality of angular direction positions to/from a fluid flowing through a luminal organ in vivo, and to output an echo data array with respect to each ultrasonic beam;
a first calculation portion which calculates the flow rate regarding the ultrasonic beam direction component of the fluid, on the basis of the echo data array;
a detection portion which obtains B mode images of the luminal organ at a plurality of time points on the basis of the repeatedly obtained echo data arrays, and on the basis of the B mode images at the plurality of time points, detects motion velocities of the wall on one side and the wall on the other side of the luminal organ at a plurality of angular directions; and
a second calculation portion which obtains a first integral result $V^-_\theta$ as a calculated value of a flow rate regarding a component of the fluid in the direction perpendicular to the ultrasonic beam direction, the first integral result being obtained by integrating the equation of continuity relating to flow rate information regarding a component of the fluid in the direction perpendicular to the ultrasonic beam direction and flow rate information regarding a component of the fluid in the ultrasonic beam direction, from one side of the liminal organ to a position of interest (r, $\theta$) at which a flow rate is to be obtained, using the motion velocity of the wall on the one side detected by the detection portion as a boundary condition for integration,
obtains a second integral result $V^+_\theta$ as a calculated value of a flow rate regarding a component of the fluid in the direction perpendicular to the ultrasonic beam direction, the second integral result being obtained by integrating the equation of continuity relating to the flow rate information regarding the component of the fluid in the direction perpendicular to the ultrasonic beam direction and the flow rate information regarding the component of the fluid in the ultrasonic beam direction, from the other side of the liminal organ to the position of interest (r, $\theta$) at which a flow rate is to be obtained, using the motion velocity of the wall of the other side detected by the detection portion as a boundary condition for integration,
calculates $V_\theta(r,\theta) = w \cdot V^-_\theta + (1-w) \cdot V^+_\theta$ using the first integral result $V^-_\theta$, the second integral result $V^+_\theta$, and the weight w, to obtain a calculated value $V_\theta(r,\theta)$ as a flow rate regarding the component of the fluid in the direction perpendicular to the ultrasonic beam direction;
wherein the weight w is proportional to a distance d from the wall on the one side, at least until a predetermined distance from the wall on the one side, and is proportional to a distance d' from the wall on the other side until a predetermined distance from the wall on the other side.

2. A fluid flow rate detection device according to claim 1, wherein the weight w is a value in proportion to a distance d from the wall of the one side.

* * * * *